(12) United States Patent
Larichev et al.

(10) Patent No.: US 8,859,799 B1
(45) Date of Patent: Oct. 14, 2014

(54) PARTIALLY FLUORINATED PHOSPHATES

(71) Applicant: E I du Pont de Nemours and Company, Wilmington, DE (US)

(72) Inventors: Roman B Larichev, Wilmington, DE (US); Xianjun Meng, Hockessin, DE (US); Allison Mary Yake, Landenberg, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 14/055,927

(22) Filed: Oct. 17, 2013

(51) Int. Cl.
  *C07F 9/02* (2006.01)
  *C07F 9/141* (2006.01)
(52) U.S. Cl.
  CPC .................................. *C07F 9/1418* (2013.01)
  USPC ......................................................... 558/175
(58) Field of Classification Search
  CPC ..... C07F 9/1651; C07F 9/4075; C07F 9/2408
  See application file for complete search history.

(56) References Cited

U.S. PATENT DOCUMENTS

| | | | |
|---|---|---|---|
| 2,988,537 A | 6/1961 | Wiley | |
| 3,540,126 A | 11/1970 | Chang | |
| 3,660,360 A | 5/1972 | Dilip et al. | |
| 3,717,679 A | 2/1973 | Thompson et al. | |
| 3,781,370 A | 12/1973 | Anello et al. | |
| 3,884,879 A | 5/1975 | Kleiner et al. | |
| 3,952,066 A | 4/1976 | Glickman et al. | |
| 3,952,075 A | 4/1976 | Nakamura et al. | |
| 4,906,792 A | 3/1990 | Heilmann et al. | |
| 4,921,619 A | 5/1990 | Karydas | |
| 5,057,623 A | 10/1991 | Kai et al. | |
| 5,091,550 A | 2/1992 | Falk et al. | |
| 5,132,445 A | 7/1992 | Falk et al. | |
| 5,157,159 A | 10/1992 | Janulis et al. | |
| 5,608,116 A | 3/1997 | Halling et al. | |
| 5,929,290 A | 7/1999 | Komiya et al. | |
| 7,473,658 B2 | 1/2009 | Acosta et al. | |
| 7,589,234 B2 | 9/2009 | Morita et al. | |
| 8,067,329 B2 | 11/2011 | Moloy | |
| 2008/0113573 A1 | 5/2008 | Acosta | |
| 2010/0168300 A1 | 7/2010 | Dams et al. | |

FOREIGN PATENT DOCUMENTS

| | | | |
|---|---|---|---|
| DE | 2052579 A | 10/1970 | |
| DE | 2333935 A1 | 1/1974 | |
| DE | 3911684 A | 4/1989 | |
| EP | 0453406 B1 | 1/1995 | |
| EP | 0363987 B1 | 2/1996 | |
| WO | 9728111 A1 | 8/1997 | |
| WO | 2005003075 A1 | 1/2005 | |
| WO | 2008147796 A1 | 12/2008 | |

OTHER PUBLICATIONS

Gervits et al., Oxyethylation of a,a Dihydroperfluoro alcohols, Translated from Izvestiya Akademil Nauk SSSR, No. 10, pp. 2256-2260, 1974.
Krespan et al., Generation and capture of functionalized fluorocarbions, Journal American Chemical Society, 1984, 5544-5546.
Honda et al., in Macromolecules, 2005, 38, 5699-5705.
Zerevitinov, Th., Quantitative Determination of the Active Hydrogen in Organic Compounds, Berichte der Deutschen Chemischen Gesellschaft, 1908, 41, 2233-43.
C. R. Martens in "Emulsion and Water-Soluble Paints and Coatings" (Reinhold Publishing Corporation, New York, NY, 1965).
A. W. Adamson in the Physical Chemistry of Surfaces, Fifth Edition, Wiley & Sons, New York, NY, 1990.
R. H. Dettre et al. in "Wettability", Ed. by J. C. Berg, Marcel Dekker, New York, NY, 1993.

*Primary Examiner* — Sun Jae Yoo

(57) ABSTRACT

The present invention relates to a compound of formula (1), or mixtures thereof:

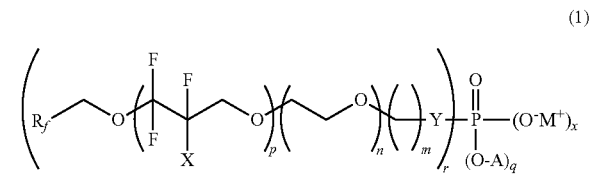

wherein $R_f$, X, Y, A, p, m, n, r, q, x, M, $R^1$, $R^2$, Z, a, and $R^6$ are defined herein; wherein at least one of p or m is a positive integer; provided that, when q is 0, r is (3−x), and when q is 1, r and x are each 1; provided that, if n is greater than 2, then p is 1; provided that, if m is 0 then Y is a single bond, and if m is a positive integer then Y is O; and provided that when $R^1$ is greater than 8 carbons, the ratio of hetero atoms to carbon atoms is at least 1:2.

12 Claims, No Drawings

PARTIALLY FLUORINATED PHOSPHATES

FIELD OF THE INVENTION

The field of invention is related to partially fluorinated phosphates and the use of partially fluorinated phosphates in coating compositions to impart surface effects to the coating compositions or to substrates coated with such compositions.

BACKGROUND OF THE INVENTION

Mixed fluorinated phosphate compounds are commonly prepared with long chain fluorinated alcohols or a mix of long chain fluorinated alcohols. These alcohols are expensive and in short supply.

Honda et al., in Macromolecules, 2005, 38, 5699-5705 show that for perfluoroalkyl chains of 8 carbons or greater, orientation of the perfluoroalkyl groups is maintained in a parallel configuration, while reorientation occurs for such chains having 6 carbon atoms or less. Such reorientation decreases surface properties such as receding contact angle. Thus, shorter chain perfluoroalkyls have traditionally not been successful commercially.

Brace and Mackenzie, in U.S. Pat. No. 3,083,224, describe mixed fluoroalkyl phosphates having the formula $[C_mF_{2m+1}C_nH_{2n}O]_yPO(OM)_{3-y}$ where m is 4 to 12, n is 1 to 16, and y is averaged to be 1.0 to 2.5. Brace and Mackenze describe their use as an oil repellent, particularly when y is 2.

It is desirable to improve surfactant performance, such as lowering the surface tension of a coating composition, while using less fluorine and while using a more selective and efficient synthetic process. It is also desirable to impart surface effects to coated surfaces, including increased blocking resistance, increased oil and water repellency, increased soil and stain resistance, increased contact angle, and increased wetting and leveling of a coating.

SUMMARY OF INVENTION

The present invention relates to a compound of formula (1), or mixtures thereof:

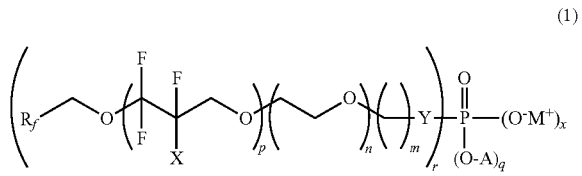

(1)

wherein $R_f$ is $C_1$ to $C_6$ linear or branched fluoroalkyl; X is F or Cl; Y is O or a single bond; A is —$R^1OH$ or $ZR^2$; p is 0 to 1; m is 0 or 2 to 10; n is 0 to 30; r is 1 or (3–x); q is 0 or 1; x is 1 to 2; M is H, a Group I metal, an ammonium alkanol, an ammonium cation $(NH_zR^3_y)^+$, or an ammonium cation $(NH_2R^4R^5)^+$; wherein $R^3$ is a $C_1$ to $C_4$ alkyl, z is 1 to 4, y is 0 to 3, z+y is 4; $R^4$ and $R^5$ are independently H or linear or branched organic groups containing at least one carboxylate moiety and one amino moiety, and $R^4$ and $R^5$ are independently optionally substituted, interrupted, or both with oxygen, sulfur, or nitrogen-containing moieties, or with cyclic, alkyl, or aryl moieties containing up to 10 carbon atoms; $R^1$ is a $C_2$ to $C_{60}$ linear or branched alkylene group optionally interrupted by hetero atoms selected from the group consisting of an oxygen, sulfur, or nitrogen atom; a cyclic alkyl; or a $C_6$ to $C_{10}$ aryl; $R^2$ is a linear, branched, or cyclic alkyl or a $C_6$ to $C_{10}$ aryl; Z is —$(CH_2CHR^6O)_a$; a is 1 to 20; $R^6$ is H, $CH_3$, or $CH_2CH_3$; wherein at least one of p or m is a positive integer; provided that, when q is 0, r is (3–x), and when q is 1, r and x are each 1; provided that, if n is greater than 2, then p is 1; provided that, if m is 0 then Y is a single bond, and if m is a positive integer then Y is O; and provided that when $R^1$ is greater than 8 carbons, the ratio of hetero atoms to carbon atoms is at least 1:2.

The invention also relates to a method for lowering the surface tension of coating compositions comprising contacting said coating compositions with one or more compounds of formula (1) wherein $R_f$, X, Y, A, p, m, n, r, q, x, M, $R^1$, $R^2$, Z, a, and $R^6$ are defined as above; wherein at least one of p or m is a positive integer; provided that, when q is 0, r is (3–x), and when q is 1, r and x are each 1; provided that, if n is greater than 2, then p is 1; provided that, if m is 0 then Y is a single bond, and if m is a positive integer then Y is O; and provided that when $R^1$ is greater than 8 carbons, the ratio of hetero atoms to carbon atoms is at least 1:2.

The invention further relates to a method of imparting surface effects to substrates comprising contacting all of a portion of a surface of the substrate with a coating composition comprising one or more compounds of formula (1) wherein $R_f$, X, Y, A, p, m, n, r, q, x, M, $R^1$, $R^2$, Z, a, and $R^6$ are defined as above; wherein at least one of p or m is a positive integer; provided that, when q is 0, r is (3–x), and when q is 1, r and x are each 1; provided that, if n is greater than 2, then p is 1; provided that, if m is 0 then Y is a single bond, and if m is a positive integer then Y is O; and provided that when $R^1$ is greater than 8 carbons, the ratio of hetero atoms to carbon atoms is at least 1:2.

DETAILED DESCRIPTION OF INVENTION

Hereinafter trademarks are designated by upper case.

The field of invention is related to partially fluorinated phosphates and the use of partially fluorinated phosphates in coating compositions to impart surface effects to the coatings or to substrates coated with such compositions. The present invention also relates to a method for lowering the surface tension of coating compositions. The present invention further relates to a method of imparting surface effects to substrates using a coating composition.

A method for lowering the surface tension of coating compositions comprising contacting said coating compositions with one or more compounds of formula (1):

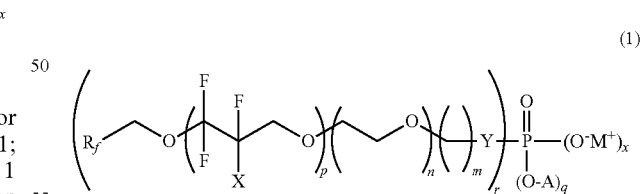

(1)

wherein $R_f$ is $C_1$ to $C_6$ linear or branched fluoroalkyl; X is F or Cl; Y is O or a single bond; A is —$R^1OH$ or $ZR^2$; p is 0 to 1; m is 0 or 2 to 10; n is 0 to 30; r is 1 or (3–x); q is 0 or 1; x is 1 to 2; M is H, a Group I metal, an ammonium alkanol, an ammonium cation $(NH_zR^3_y)^+$, or an ammonium cation $(NH_2R^4R^5)^+$; wherein $R^3$ is a $C_1$ to $C_4$ alkyl, z is 1 to 4, y is 0 to 3, z+y is 4; $R^4$ and $R^5$ are independently H or linear or branched organic groups containing at least one carboxylate moiety and one amino moiety, and $R^4$ and $R^5$ are independently optionally substituted, interrupted, or both with oxygen, sulfur, or nitrogen-containing moieties, or with cyclic, alkyl, or aryl moieties containing up to 10 carbon atoms; $R^1$ is a $C_2$ to $C_{60}$ linear or branched alkylene group optionally interrupted by hetero atoms selected from the group consisting of an oxygen, sulfur, or nitrogen atom; a cyclic alkyl; or a $C_6$ to $C_{10}$ aryl; $R^2$ is a linear, branched, or cyclic alkyl or a $C_6$ to $C_{10}$ aryl; Z is —$(CH_2CHR^6O)_a$; a is 1 to 20; $R^6$ is H, $CH_3$, or $CH_2CH_3$; wherein at least one of p or m is a positive integer; provided that, when q is 0, r is (3–x), and when q is 1, r and x are each 1; provided that, if n is greater than 2, then p is 1; provided that, if m is 0 then Y is a single bond, and if m is a positive integer then Y is O; and provided that when $R^1$ is greater than 8 carbons, the ratio of hetero atoms to carbon atoms is at least 1:2.

Partially fluorinated phosphates of formula (1), as defined above wherein q is 0, can be prepared by reacting partially fluorinated alcohols of formula (2):

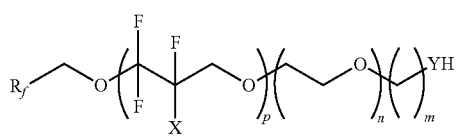

(2)

wherein $R_f$ is $C_1$ to $C_6$ linear or branched fluoroalkyl, X is F or Cl, Y is O or a single bond, p is 0 to 1, m is 0 or 2 to 10, and n is 0 to 30, wherein at least one of p or m is a positive integer; provided that, if n is greater than 2, then p is 1; provided that, if m is 0 then Y is a single bond, and if m is a positive integer then Y is O; with phosphorus pentoxide ($P_2O_5$) to form mixed acidic phosphates of formula (1) wherein q is 0 and M is H. The mol ratio of the fluorinated alcohol to $P_2O_5$ is from about 2.0-3.0:1, preferably about 2.3-3.0:1. The mixed acidic phosphates can be then neutralized with an aqueous base, such as ammonium hydroxide and/or amino acid, to form a water soluble mixed phosphate ester of formula (1) wherein q is 0 and M is a Group I metal, an ammonium alkanol, an ammonium cation $(NH_zR^3_y)^+$, or an ammonium cation $(NH_2R^4R^5)^+$; wherein $R^3$ is a $C_1$ to $C_4$ alkyl, z is 1 to 4, y is 0 to 3, z+y is 4; $R^4$ and $R^5$ are independently H or linear or branched organic groups containing at least one carboxylate moiety and one amino moiety, and $R^4$ and $R^5$ are independently optionally substituted, interrupted, or both with oxygen, sulfur, or nitrogen-containing moieties, or with cyclic, alkyl, or aryl moieties containing up to 10 carbon atoms, $R^1$ is a $C_2$ to $C_{60}$ linear or branched alkyl group optionally interrupted by hetero atoms selected from the group consisting of an oxygen, sulfur, or nitrogen atom; a cyclic alkyl; or a $C_6$ to $C_{10}$ aryl. In this reaction, a mixture of compounds If formed, where x is 1 and 2. Alternatively, phosphorus oxychloride ($POCl_3$) may be used instead of phosphorus pentoxide, according to conventional methods, to form partially fluorinated phosphates of formula (1), wherein q is 0, with increased selectivity of x.

Partially fluorinated phosphates of formula (1), as defined above wherein q is 1 and A is —$R^1OH$, can be prepared by reacting $P_2O_5$ with a partially fluorinated alcohol of formula (2), as defined above, followed by the addition of hydrocarbon diol or poly(glycol) to form mixed acidic phosphates of formula (1) wherein q is 1, A is —$R^1OH$, and M is H. Typically the phosphorus pentoxide is added to the fluorinated alcohol at elevated temperature. The mol ratio of the fluorinated alcohol to $P_2O_5$ is from about 0.4-1.6:1, preferably about 1:1. A diol or poly(glycol) is then added to the reaction mixture. The mole ratio of diol or poly(glycol) to $P_2O_5$ is from about 1.4-2.6:1. The mixed acidic phosphates can be then neutralized with an aqueous base, such as ammonium hydroxide and/or amino acid, to form a phosphate of formula (1) wherein q is 1, A is —$R^1OH$, and M is a Group I metal, an ammonium alkanol, an ammonium cation $(NH_zR^3_y)^+$, or an ammonium cation $(NH_2R^4R^5)^+$; wherein $R^3$ is a $C_1$ to $C_4$ alkyl, z is 1 to 4, y is 0 to 3, z+y is 4; $R^4$ and $R^5$ are independently H or linear or branched organic groups containing at least one carboxylate moiety and one amino moiety, and $R^4$ and $R^5$ are independently optionally substituted, interrupted, or both with oxygen, sulfur, or nitrogen-containing moieties, or with cyclic, alkyl, or aryl moieties containing up to 10 carbon atoms, $R^1$ is a $C_2$ to $C_{60}$ linear or branched alkyl group optionally interrupted by hetero atoms selected from the group consisting of an oxygen, sulfur, or nitrogen atom; a cyclic alkyl; or a $C_6$ to $C_{10}$ aryl. Alternatively, phosphorus oxychloride ($POCl_3$) may be used instead of phosphorus pentoxide, according to conventional methods, to form partially fluorinated phosphates of formula (1) wherein q is 1 and A is —$R^1OH$.

Partially fluorinated phosphates of formula (1), defined above wherein q is 1 and A is $ZR^2$, can be prepared by reacting $P_2O_5$ with a fluorinated alcohol of formula (2), defined above, followed by the addition of hydrocarbon alcohol to form mixed acidic phosphates of formula (1) wherein q is 1, A is $ZR^2$, and M is H. Typically the phosphorus pentoxide is added to the fluorinated alcohol at elevated temperature. The mol ratio of the fluorinated alcohol to $P_2O_5$ is from about 0.4-1.6:1, preferably about 1:1. A hydrocarbon alcohol is then added to the reaction mixture. The mole ratio of hydrocarbon alcohol to $P_2O_5$ is from about 1.4-2.6:1. The mixed acidic phosphates can then optionally be neutralized with an aqueous base, such as ammonium hydroxide and/or amino acid, to form a phosphate of formula (1) wherein q is 1, A is $ZR^2$, and M is a Group I metal, an ammonium alkanol, an ammonium cation $(NH_zR^3_y)^+$, or an ammonium cation $(NH_2R^4R^5)^+$; wherein $R^3$ is a $C_1$ to $C_4$ alkyl, z is 1 to 4, y is 0 to 3, z+y is 4; $R^4$ and $R^5$ are independently H or linear or branched organic groups containing at least one carboxylate moiety and one amino moiety, and $R^4$ and $R^5$ are independently optionally substituted, interrupted, or both with oxygen, sulfur, or nitrogen-containing moieties, or with cyclic, alkyl, or aryl moieties containing up to 10 carbon atoms, $R^1$ is a $C_2$ to $C_{60}$ linear or branched alkyl group optionally interrupted by hetero atoms selected from the group consisting of an oxygen, sulfur, or nitrogen atom; a cyclic alkyl; or a $C_6$ to $C_{10}$ aryl. Alternatively, phosphorus oxychloride ($POCl_3$) may be used instead of phosphorus pentoxide, according to conventional methods, to form partially fluorinated phosphates of formula (1) wherein q is 1 and A is $ZR^2$.

The partially fluorinated alcohols of formula (2) can be prepared by multiple methods, using the starting material $R_fCH_2OH$, wherein $R_f$ is $C_1$ to $C_6$ linear or branched fluoroalkyl, preferably $C_1$ to $C_3$ linear fluoroalkyl, or mixtures thereof.

One process includes forming partially fluorinated alcohols of formula (2a), a selection from formula (2) where $R_f$ is $C_1$ to $C_6$ linear or branched fluoroalkyl, X is F or Cl, Y is a single bond, p is 1, m is 0, and n is 0:

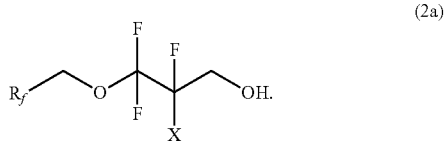

(2a)

In this process, the partially fluorinated alcohol is prepared by a) contacting an alkali metal hydride with a fluorinated alcohol of formula $R_fCH_2OH$, wherein $R_f$ is $C_1$ to $C_6$ linear or branched fluoroalkyl, to produce an alkoxide catalyst $R_fCH_2O^-$, b) contacting $R_fCH_2OH$ with (i) formic acid to produce a partially fluorinated formate, (ii) alkyl chloroformate to produce a mixed partially fluorinated carbonate, or (iii) phosgene, diphosgene, or triphosgene to produce a symmetrical partially fluorinated carbonate, c) contacting the partially fluorinated formate of step (b)(i), mixed partially fluorinated carbonate of step (b) (ii), or symmetrical partially fluorinated carbonate of step (b) (iii) with $CF_2=CFX$, wherein X is F or Cl, in the presence of the alkoxide catalyst $R_fCH_2O^-$ to yield, respectively, a partially fluorinated aldehyde (i), partially fluorinated ester (ii), or partially fluorinated carboxylic acid (iii), d) contacting the partially fluorinated carboxylic acid of step (c) (iii) with an organic alcohol to form a partially fluorinated ester, and e) contacting (i) the partially fluorinated aldehyde of step (c) (i), (ii) the partially fluorinated ester of step (c) (ii), or (iii) the partially fluorinated ester of step (d) with a reducing agent to form the compound of formula (2a). Preferably, the same starting alcohol used in step a) to form the catalyst is also used in step b) to form the partially fluorinated formate, mixed partially fluorinated carbonate, or symmetrical partially fluorinated carbonate. The partially fluorinated carboxylic acid of step (c) (iii) is preferably formed by hydrolyzing the direct product of $CF_2=CFX$ and the symmetrical partially fluorinated carbonate of step (b) (iii).

An additional step, f) contacting the compound of formula (2a) with an alcohol of the formula $J(CH_2)_tOH$ in the presence of a base, where J is a halogen and t is 2-10, or ethylene oxide in the presence of a catalyst, can be employed to form the compound of formula (2b) or (2d):

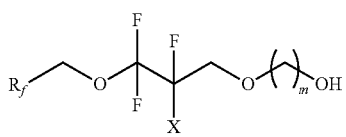
(2b)

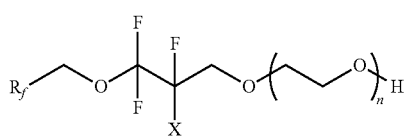
(2d)

Formula (2b) represents a preferred compound of formula (2), where $R_f$ is $C_1$ to $C_6$ linear or branched fluoroalkyl, X is F or Cl, Y is O, p is 1, m is 3 to 10, preferably 3 to 8 and more preferably 3 to 6, and n is 0. Formula (2d) represents a preferred compound of formula (2), where $R_f$ is $C_1$ to $C_6$ linear or branched fluoroalkyl, X is F or Cl, Y is a single bond, p is 1, m is 0, and n is 1 to 30, preferably 1 to 12.

The alkali metal hydride of step a) can be any alkali metal hydride conventionally used in the art, but is preferably selected from the group consisting of NaH, KH, and $CaH_2$. The alkyl chloroformate of step (b) (ii) is preferably $C_1$ to $C_6$ alkyl chloroformate, and more preferably methyl chloroformate. Preferred organic alcohols for step d) include ethanol and methanol. The reducing agent of step e) can be any reducing agent conventionally used in the art but is preferably selected from the group consisting of $LiAlH_4$ and $NaBH_4$.

The partially fluorinated alcohols of formula (2) can also be prepared by contacting an alcohol of the formula $R_fCH_2OH$, wherein $R_f$ is $C_1$ to $C_6$ linear or branched fluoroalkyl, with an alcohol of formula $J(CH_2)_tOH$, where J is a halogen and t is 3-10, in the presence of a base. In this case, the resulting alcohol is represented by formula (2c):

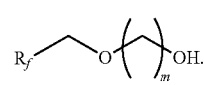
(2c)

Formula (2c) represents a preferred compound of formula (2), where $R_f$ is $C_1$ to $C_6$ linear or branched fluoroalkyl, Y is O, p is 0, m is 3 to 10, preferably 3 to 8 and more preferably 3 to 6, and n is 0.

The base used to form the alcohol of formula (2b) or (2c) can be any base conventionally used in the art, but is preferably selected from the group consisting of NaH, KOH, NaOH, $Na_2CO_3$, and $Cs_2CO_3$.

The partially fluorinated alcohols of formula (2) can also be prepared by contacting an alcohol of the formula $R_fCH_2OH$, wherein $R_f$ is $C_1$ to $C_6$ linear or branched fluoroalkyl, with ethylene oxide, in the presence of a catalyst. In this case, the resulting alcohol is represented by formula (2e):

(2e)

Formula (2e) represents a preferred compound of formula (2), where $R_f$ is $C_1$ to $C_6$ linear or branched fluoroalkyl, Y is a single bond, p is 0, m is 0, and n is 1 to 2.

The catalyst used to form the alcohols of formula (2d) or (2e) can be any catalyst conventionally used in the art, but is preferably selected from the group consisting of NaH, KOH, NaOH, $Cs_2CO_3$, and a boron-based catalyst. The term "boron-based catalyst" is hereby defined as a mixture of trialkyl borate $B(OR^{20})_3$ and a halide source LE, wherein $R^{20}$ is a linear, branched, cyclic, or aromatic hydrocarbyl group, optionally substituted, having from 1 to 30 carbon atoms; L is a cation of the alkali metals Na+, K+, Li+ or a cation of an alkyl tertiary amine or alkyl tertiary phosphorus; and E is fluoride, bromide, or iodide. Trialkyl borates are typically prepared in situ by reacting boric acid or sodium borohydride with the alcohol to be ethoxylated. The base compounds, as well as the starting materials for borate synthesis, are readily available from Sigma Aldrich, St. Louis, Mo. The borate/halide catalyst system is described in detail in U.S. Pat. No. 8,067,329, herein incorporated by reference.

The base used to neutralize the mixed acidic phosphates to form the mixed phosphate esters of the invention provide cation M, such as a Group I metal, an ammonium alkanol, an ammonium cation $(NH_zR^3{}_y)^+$, or an ammonium cation $(NH_2R^4R^5)^+$; wherein $R^3$ is a $C_1$ to $C_4$ alkyl, z is 1 to 4, y is 0 to 3, z+y is 4; $R^4$ and $R^5$ are independently H or linear or branched organic groups containing at least one carboxylate moiety and one amino moiety, and $R^4$ and $R^5$ are independently optionally substituted, interrupted, or both with oxygen, sulfur, or nitrogen-containing moieties, or with cyclic, alkyl, or aryl moieties containing up to 10 carbon atoms, $R^1$ is a $C_2$ to $C_{60}$ linear or branched alkyl group optionally interrupted by hetero atoms selected from the group consisting of an oxygen, sulfur, or nitrogen atom; a cyclic alkyl; or a $C_6$ to $C_{10}$ aryl. Preferred bases are selected from Group I metal base salts, such as sodium hydroxide, potassium hydroxide, and lithium hydroxide; ammonium alkanols such as diethanolamine; ammonium hydroxide; ammonium alkyls; and amino acids, such as lysine and arginine.

The base is added as an aqueous solution to form a final product comprising aqueous water-soluble mixed phosphate ester, and the mixed phosphate ester can be diluted to a desired active ingredient content, based on solids content of the mixed phosphate ester. Cosolvents may be employed as desired, including but not limited to organic alcohols, such as isopropanol or methanol.

A surfactant can optionally be added in an amount of from about 1% to about 3% by weight. Any of a variety of surfactants can be employed, such as TERGITOL available from Sigma Aldrich, St. Louis, Mo.

Hydrocarbon diols useful in the synthesis of compounds of Formula (1), wherein q is 1 and A is —$R^1OH$, include $C_2$ to $C_{60}$ straight and branched chain alcohols, optionally having one or two double bonds. Examples include 1,3-propanediol; propylene glycol (1,2-propanediol); di(ethylene glycol); tri(ethylene glycol); tetra(ethylene glycol); poly(ethylene glycol)s [PEG(OH)$_2$], preferably having from about 4 to about 20 repeat units, and more preferably from about 5 to about 15 repeat units; poly(ethylene glycol)-polypropylene glycol-poly(ethylene glycol) triblock polymers [PEG-PPG-PEG-(OH)$_2$]; and random copolymers of ethylene oxide and propylene oxide, preferably with a molecular weight of from about 200 to about 1250. Poly(1,3-propanediol)s are available from E. I. du Pont de Nemours and Company, Wilmington, Del. Polyethylene glycols with nominal molecular weights of 200 to 2000 are available from Aldrich Chemical Company, St. Louis, Mo. Tri-block copolymers of polyethylene oxide and polypropylene oxide (PEG-PPG-PEG) are available from BASF, Mount Olive, N.J.

Hydrocarbon alcohols useful in the synthesis of compounds of formula (1), wherein q is 1 and A is $ZR^2$, include alkoxylated alcohols of the formula $HO(CH_2CHR^6O)_aR^2$, where a is 1 to 20, $R^2$ is a linear, branched, or cyclic alkyl or a $C_6$ to $C_{10}$ aryl, and $R^6$ is H, $CH_3$, or $CH_2CH_3$. Any such alcohols may be used, including poly(ethylene glycol) methyl ethers, polypropylene glycol) methyl ethers, and fatty acid alcohol alkoxylates. Fatty acid alcohol alkoxylates are conventionally made by alkoxylating a fatty acid alcohol. Preferred alcohols include fatty acid ethoxylates, where $R^2$ is a linear $C_6$ to $C_{12}$ alkyl, preferably a linear $C_8$ to $C_{10}$ alkyl.

These phosphates of formula (1), prepared from partially fluorinated alcohols of formula (2), have several uses as a surfactant.

The invention also relates to a method for lowering the surface tension of coating compositions comprising contacting said coating compositions with one or more compounds of formula (1) wherein $R_f$, X, Y, A, p, m, n, r, q, x, M, $R^1$, $R^2$, Z, a, and $R^6$ are defined as above; wherein at least one of p or m is a positive integer; provided that, when q is 0, r is (3−x), and when q is 1, r and x are each 1; provided that, if n is greater than 2, then p is 1; provided that, if m is 0 then Y is a single bond, and if m is a positive integer then Y is O; and provided that when $R^1$ is greater than 8 carbons, the ratio of hetero atoms to carbon atoms is at least 1:2. The present invention also comprises a coating composition treated in accordance with the method of lowering the surface tension.

In the method of the present invention, contacting the partially fluorinated phosphates, as defined above, with the coating composition is typically achieved by simply blending with or adding the phosphates of the present invention to the coating composition. The contacting of the phosphates of the present invention to the coating composition can occur prior to applying the coating composition to a substrate, or can occur after applying the coating composition to a substrate. This contacting step with the partially fluorinated phosphates of the invention can also serve to increase wetting and leveling in the coating composition. In the present invention, a low concentration of about 0.5% by weight of phosphates of the present invention is sufficient to lower surface tension of a coating composition to less than about 22 dyne/cm$^2$, with some phosphates lowering the surface tension to less than about 19 dyne/cm$^2$.

Suitable coating compositions, referred to herein by the term "coating composition" or "coating base", include a composition, typically a liquid formulation, of an alkyd coating, Type I urethane coating, unsaturated polyester coating, or water-dispersed coating, and are applied to a substrate for the purpose of creating a lasting film on a substrate surface. These are conventional paints, stains, polishing agents, floor finishes, floor polishes, and similar coating compositions.

By the term "alkyd coating" as used herein is meant a conventional liquid coating based on alkyd resins, typically a paint, clear coating, or stain. The alkyd resins are complex branched and cross-linked polyesters containing unsaturated aliphatic acid residues. Conventional alkyd coatings utilize, as the binder or film-forming component, a curing or drying alkyd resin. Alkyd resin coatings contain unsaturated aliphatic acid residues derived from drying oils. These resins spontaneously polymerize in the presence of oxygen or air to yield a solid protective film. The polymerization is termed "drying" or "curing" and occurs as a result of autoxidation of the unsaturated carbon-carbon bonds in the aliphatic acid component of the oil by atmospheric oxygen. When applied to a surface as a thin liquid layer of formulated alkyd coating, the cured films that form are relatively hard, non-melting, and substantially insoluble in many organic solvents that act as solvents or thinners for the un-oxidized alkyd resin or drying oil. Such drying oils have been used as raw materials for oil-based coatings and are described in the literature.

By the term "urethane coating" as used hereinafter is meant a conventional liquid coating based on Type I urethane resins, typically a paint, clear coating, or stain. Urethane coatings typically contain the reaction product of a polyisocyanate, usually toluene diisocyanate, and a polyhydric alcohol ester of drying oil acids. Urethane coatings are classified by ASTM D-1 into five categories. Type I urethane coatings contain a pre-reacted autoxidizable binder as described in Surface Coatings Vol. I. These are also known as uralkyds, urethane-modified alkyds, oil-modified urethanes, urethane oils, or urethane alkyds, are the largest volume category of polyurethane coatings and include paints, clear coatings, or stains. The cured coating is formed by air oxidation and polymerization of the unsaturated drying oil residue in the binder.

By the term "unsaturated polyester coating" as used hereinafter is meant a conventional liquid coating based on unsaturated polyester resins, dissolved in monomers and containing initiators and catalysts as needed, typically as a paint, clear coating, or gel coat formulation. Unsaturated polyester resins contain as the unsaturated prepolymer the product obtained from the condensation polymerization of a glycol, such as 1,2-propylene glycol or 1,3-butylene glycol, with an unsaturated acid such as maleic (or of maleic and a saturated acid, e.g., phthalic) in the anhydride form. The unsaturated prepolymer is a linear polymer containing unsaturation in the chain. This is dissolved in a suitable monomer, for instance styrene, to produce the final resin. The film is produced by copolymerization of the linear polymer and monomer by means of a free radical mechanism. The free radicals can be generated by heat, or more usually by addition of a peroxide, such as benzoyl peroxide, separately packaged and added before use. Such coating compositions are frequently termed "gel coat" finishes. For curing coatings at room temperature, the decomposition of peroxides into free radicals is catalyzed by certain metal ions, usually cobalt. The solutions of peroxide and cobalt compound are added separately to the mix and well stirred before application. The unsaturated polyester resins that cure by a free radical mechanism are also suited to irradiation curing using, for instance, ultraviolet light. This form of cure, in which no heat is produced, is particularly suited to films on wood or board. Other radiation sources, for instance electron-beam curing, are also used.

By the term "water-dispersed coatings" as used herein is meant coatings intended for the decoration or protection of a substrate composed of water as an essential dispersing component such as an emulsion, latex, or suspension of a film-forming material dispersed in an aqueous phase. "Water-dispersed coating" is a general classification that describes a number of formulations and includes members of the above described classifications as well as members of other classifications. Water-dispersed coatings in general contain other common coating ingredients. Water-dispersed coatings are exemplified by, but not limited to, pigmented coatings such as latex paints, automotive base coats, industrial maintenance paints, unpigmented coatings such as clear wood sealers, stains, and finishes, industrial and automotive high gloss clear coatings, coatings for masonry and cement, and water-based asphalt emulsions. A water dispersed coating optionally contains surfactants, protective colloids and thickeners, pigments and extender pigments, preservatives, fungicides, freeze-thaw stabilizers, antifoam agents, agents to control pH, coalescing aids, and other ingredients. For latex paints the film forming material is a latex polymer of acrylate acrylic, vinyl-acrylic, vinyl, or a mixture thereof. Such water-dispersed coating compositions are described by C. R. Martens in "Emulsion and Water-Soluble Paints and Coatings" (Reinhold Publishing Corporation, New York, N.Y., 1965).

By the term "dried coating" as used herein is meant the final decorative and/or protective film obtained after the coating composition has dried, set or cured. Such a final film can be achieved by, for non-limiting example, curing, coalescing, polymerizing, interpenetrating, radiation curing, UV curing or evaporation. Final films can also be applied in a dry and final state as in dry coating.

Floor waxes, polishes, or finishes are generally water-based or solvent-based polymer emulsions. The phosphates of the present invention used in the methods of the present invention are suitable for use in such floor finishes. Commercially available floor finish compositions typically are aqueous emulsion-based polymer compositions comprising one or more organic solvents, plasticizers, coating aides, anti-foaming agents, surfactants, polymer emulsions, metal complexing agents, and waxes. The particle size range and solids content of the polymer are usually controlled to control the product viscosity, film hardness and resistance to deterioration. Polymers containing polar groups function to enhance solubility and may also act as wetting or leveling agents providing good optical properties such a high gloss and distinctness of reflected image.

Preferred polymers for use in floor finishes include acrylic polymers, polymers derived from cyclic ethers, and polymers derived from vinyl substituted aromatics. Acrylic polymers include various poly(alkyl acrylates), poly(alkyl methacrylates), hydroxyl substituted poly(alkyl acrylates) and poly(alkyl methacrylates). Commercially available acrylic copolymers used in floor finishes include, for example, methyl methacrylate/butyl acrylate/methacrylic acid (MMA/BA/MAA) copolymers; methyl methacrylate/butyl acrylate/acrylic acid (MMA/BA/AA) copolymers, and the like. Commercially available styrene-acrylic copolymers include styrene/methyl methacrylate/butyl acrylate/methacrylic acid (S/MMA/BA/MMA) copolymers; styrene/methyl methacrylate/butyl acrylate/acrylic acid (S/MMA/BA/AA) copolymers; and the like. Polymers derived from cyclic ethers usually contain 2 to 5 carbon atoms in the ring with optional alkyl groups substituted thereon. Examples include various oxiranes, oxetanes, tetrahydrofurans, tetrahydropyrans, dioxanes, trioxanes, and caprolactone. Polymers derived from vinyl substituted aromatics include for example those made from styrenes, pyridines, conjugated dienes, and copolymers thereof. Polyesters, polyamides, polyurethanes and polysiloxanes are also used in floor finishes.

The waxes or mixtures of waxes that are used in floor finishes include waxes of a vegetable, animal, synthetic, and/or mineral origin. Representative waxes include, for example, carnuba, candelilla, lanolin, stearin, beeswax, oxidized polyethylene wax, polyethylene emulsions, polypropylene, copolymers of ethylene and acrylic esters, hydrogenerated coconut oil or soybean oil, and the mineral waxes such as paraffin or ceresin. The waxes typically range from 0 to about 15 weight percent and preferably from about 2 to about 10 weight percent based on the weight of the finish composition.

When the coating composition is a floor finish, floor wax, or floor polish, the phosphates of the present invention as defined above are effectively introduced to the coating composition by thoroughly stirring it in at room or ambient temperature. More elaborate mixing can be employed such as using a mechanical shaker or providing heat or other methods. The phosphates of the present invention generally are added at about 0.001 weight % to about 5 weight % by dry weight of the coating composition of the invention in the wet composition. Preferably about from about 0.005 weight % to about 2 weight %, more preferably from about 0.005 weight % to about 0.5 weight %, and even more preferably from about 0.01 weight % to about 0.05 weight % is used.

Floor waxes or polishes are water-based, solvent-based and polymer. The phosphates used in the present invention are suitable for use with any of these. Water-based and polymer waxes dry to a high gloss without buffing; solvent-based wax requires vigorous buffing. Water-based wax is recommended for asphalt, vinyl, vinyl asbestos and rubber-tiled floors; solvent-based waxes produce a hard, shiny finish and are best for wood, cork and terrazzo floors. Self-polishing waxes, such as polymer or resin, will yellow or discolor and wear off in heavy traffic areas; they should be stripped off and reapplied after three or four coats.

When the coating composition is latex paints, the phosphates of formula (1), as defined above, are effectively contacted with the coating composition by thoroughly stirring it in at room or ambient temperature. More elaborate mixing can be employed such as using a mechanical shaker or providing heat or other methods. Such methods are not necessary and do not substantially improve the final composition. The phosphates of formula (1) are generally contacted with the wet paint at about 0.001 weight % to about 5 weight %, based on the active ingredient (solids) content of the mixed phosphate solution or dispersion. Preferably about 0.01 weight % to about 1 weight %, and more preferably about 0.1 weight % to about 0.5 weight % is used.

The invention further relates to a method of imparting surface effects to substrates comprising contacting all of a portion of a surface of the substrate with a coating composition comprising one or more compounds of formula (1) wherein $R_f$, X, Y, A, p, m, n, r, q, x, M, $R^1$, $R^2$, Z, a, and $R^6$ are defined as above; wherein at least one of p or m is a positive integer; provided that, when q is 0, r is (3−x), and when q is 1, r and x are each 1; provided that, if n is greater than 2, then p is 1; provided that, if m is 0 then Y is a single bond, and if m is a positive integer then Y is O; and provided that when $R^1$ is greater than 8 carbons, the ratio of hetero atoms to carbon atoms is at least 1:2. Surface effects include resistance to blocking, oil repellency, water repellency, stain resistance, dirt pickup resistance, increased contact angle, or increased wetting and leveling of the coating surface. Typically, the increase of the contact angle of the coating composition results in increased anti-blocking, oil repellency, and resistance to dirt pickup in the dried coating.

The term "resistance to dirt pickup" or "dirt pickup resistance" is used herein to mean resistance by the dried coating to soiling. It is particularly applicable to coatings exposed to weather in that the coating resists soiling from dirt, debris, mold, and other conditions encountered in normal weather throughout the year. The level of dirt pickup resistance is indicated by the measurement of advancing oil contact angle. "Blocking" is the undesirable sticking together of two coated surfaces when pressed together, or placed in contact with each other for an extended period of time, after the coating has dried. When blocking occurs separation of the surfaces can result in disruption of the coating on one or both surfaces. Thus anti-blocking, also referred to as resistance to blocking, is beneficial in many situations where two coated surfaces need to be in contact, for example on window frames. "Oil repellency" is the ability of a surface coated with a coating composition according to the method of the present invention to not allow oil globules to spread. Oil repellency is determined by measuring the advancing angle when a drop of oil is placed in contact with a surface coated with a coating composition described above for use in the above described methods of the present invention.

The contacting of the coating composition with all or a portion of a surface of the substrate is achieved by conventional means. Non-limiting examples include application by brush, cloth, pad, spray, doctor blade, or other known means.

The present invention further comprises a substrate treated according to any of the above-described methods of the present invention. One or more surfaces of the substrate have been contacted with a coating composition containing a phosphate comprising formula (1).

Typical substrates include a wide variety of surfaces on which coating compositions are normally used. These include various construction materials, typically hard surfaced materials. The hard surface substrates include porous and nonporous mineral surfaces, such as glass, stone, masonry, concrete, unglazed tile, brick, porous clay and various other substrates with surface porosity. Specific examples of such substrates include unglazed concrete, brick, tile, stone including granite, limestone and marble, grout, mortar, statuary, monuments, wood, composite materials such as terrazzo, and wall and ceiling panels including those fabricated with gypsum board. In addition plastics, metals, ceramics, and other hard surfaces are included in the present invention. These are used in the construction of buildings, siding, roads, parking ramps, driveways, floorings, fireplaces, fireplace hearths, counter tops, walls, ceilings, decks, patios, furniture, fixtures, appliances, molded articles, shaped articles, decorative articles, and other items used in interior and exterior applications.

Other substrates include fibrous substrates. Most fibrous substrates are suitable for treatment by the methods of the present invention. Such substrates include fibers, yarns, fabrics, fabric blends, textiles, carpet, rugs, nonwovens, leather and paper. The term "fiber" includes fibers and yarns, before and after spinning, of a variety of compositions and forms, and includes pigmented fibers and pigmented yarns. By "fabrics" is meant natural or synthetic fabrics, or blends thereof, composed of fibers such as cotton, rayon, silk, wool, polyester, polypropylene, polyolefins, nylon, and aramids such as "NOMEX" and "KEVLAR". By "fabric blends" is meant fabric made of two or more different fibers. Typically these blends are a combination of at least one natural fiber and at least one synthetic fiber, but also can be a blend of two or more natural fibers and/or of two or more synthetic fibers.

Shorter chain fluorinated alcohols would provide a reduction of fluorine in the resulting mixed phosphate compounds, which is desirable, while maintaining equal or superior performance. Reduction of fluorine content in the fluorinated alcohols would also reduce the cost to produce these phosphates while maintaining the performance characteristics. The present invention provides fluoroalkyl mixed phosphate compounds with low fluorine contents, and methods to increase surfactant performance and improve surface effects on a coated surface. These fluoroalkyl mixed phosphate compounds are also made from partially fluorinated alcohols that have been synthestized using a new, more selective and efficient chemical process.

MATERIALS AND TEST METHODS

Test Methods

Hereinafter, the term "active ingredient" in the final product is defined as the solids content of the phosphate surfactant solution or dispersion.

Test Method 1—Surface Tension Measurement

Surface tension was measured according to the American Society for Testing and Materials ASTM # D1331-56, using the Wilhelmy plate method on a KRUSS K11 Version 2.501 tensiometer (KRUSS USA, 5 Matthews N.C.) in accordance with instructions with the equipment. A vertical plate of known perimeter was attached to a balance, and the force due to wetting was measured. Each example to be tested was prepared as an aqueous solution based on percent of solids by weight in deionized water. Several different concentrations were prepared. Ten replicates were tested of each dilution, and the following machine settings were used: Method: Plate Method SFT; Interval: 1.0 s; Wetted length: 40.2 mm; 15 reading limit: 10; Minimum standard deviation: 2 dynes/cm; and Gr. accellearation: 9.80665 m/s$^2$.

Results were in dynes/cm (mN/m) with a Standard Deviation of less than 1 dyne/cm. The tensiometer was used according to the manufacturer's recommendations. A stock solution was prepared for the highest concentration of surfactant to be analyzed. The concentration of the solution was by weight percent of the surfactant solids in deionized water. The solutions are stirred overnight (for approximately 12 hours) to ensure complete mixing. Lower concentrations of the stock solution for each example were made by diluting the original stock solution. Lower surface tension results indicate superior performance.

Test Method 2—Blocking Resistance of Architectural Latex Paints

The test method described herein is a modification of ASTM D4946-89 —Standard Test Method for Blocking Resistance of Architectural Paints The face-to-face blocking resistance of paints to be tested was evaluated in this test. Blocking, for the purpose of this test, is defined as the undesirable sticking together of two painted surfaces when pressed together or placed in contact with each other for an extended period of time.

The phosphate surfactants were dosed into paint according to a desired active ingredient content or a desired level of total fluorine percentage. The paint, dosed with phosphate surfactant, was cast onto a polyester test panel using an applicator blade. All painted panels were protected from grease, oil, fingerprints, dust, et cetera, to avoid surface contamination that could affect blocking resistance results. Typically, results are evaluated at 24 hours after casting the paint. After the panels have been conditioned in the conditioned room as specified in the ASTM Method referenced above for the desired period of time, six squares (3.8 cm×3.8 cm) were cut out from the painted test panel. The cut sections (three pairs) were placed with the paint surfaces face-to-face for each of the paints to be tested. The cut sections (three pairs) are placed with the paint surfaces face-to-face for each of the paints to be tested. The face-to-face specimens were placed in a 50° C. oven on a marble tray. A no. 8 stopper was placed on top, with the smaller diameter in contact with the specimens, and then a 1000 g weight was placed on top of the stopper. This resulted in a pressure of 1.8 psi ($12.4 \times 10^3$ Pa) on the specimens. One weight and stopper was used for each specimen tested. After exactly 30 minutes, the stoppers and weights were taken off the test specimens which were removed from the oven and allowed to cool in the conditioned room for 30 minutes before determining resistance to blocking.

After cooling, the specimens were separated by peeling apart with a slow and steady force. The blocking resistance was rated from 0 to 10, corresponding to a subjective tack assessment (sound made upon separation of the painted specimens) or seal (complete adhesion of the two painted surfaces) as determined by the operator of the method. The specimen was put near the ear to actually hear the degree of tack. The rating system is described in Table 1. The degree of seal was estimated from the appearance of the specimens and the fraction of the paint surfaces that adhere. Paint tearing away from the test panel backing was an indication of seal. A higher number indicates better resistance to blocking.

TABLE 1

Blocking Resistance Numerical Ratings

| Blocking Resistance Numerical Ratings | Description of the Separation | Performance Description |
|---|---|---|
| 10 | No tack | Perfect |
| 9 | Trace tack | Excellent |
| 8 | Very slight tack | Very good |
| 7 | Slight tack | Good/very good |
| 6 | Moderate to slight tack | Good |
| 5 | Moderate tack | Fair |
| 4 | Very tacky-no seal | Poor to fair |
| 3 | 5 to 25% seal | Poor |
| 2 | 25 to 50% seal | Poor |
| 1 | 50 to 75% seal | Very poor |
| 0 | 75 to 100% seal | Very poor |

Test Method 3—Contact Angle

Contact angles were measured by the Sessile Drop Method, which is described by A. W. Adamson in The Physical Chemistry of Surfaces, Fifth Edition, Wiley & Sons, New York, N.Y., 1990. Additional information on the equipment and procedure for measuring contact angles is provided by R. H. Dettre et al. in "Wettability", Ed. by J. C. Berg, Marcel Dekker, New York, N.Y., 1993. In the Sessile Drop Method, a Ramè-Hart optical bench (available from Ramè-Hart Inc., 43 Bloomfield Ave., Mountain Lakes, N.J.) was used to hold the substrate in the horizontal position. The contact angle was measured at a prescribed temperature with a telescoping goniometer from the same manufacturer. Each Example to be tested was added to MAB paint according to a desired weight percentage or total fluorine percentage. A drop of test liquid was placed on a polyester scrub test panel (Leneta P-121 dull black or equivalent, Leneta Company, Mahwah, N.J.) and the tangent was precisely determined at the point of contact between the drop and the surface. An advancing angle was determined by increasing the size of the drop of liquid. The data were presented as advancing contact angles.

The relationship between organic liquid contact angles, and the cleanability and dirt retention of surfaces is described by A. W. Adamson, above. In general, higher hexadecane contact angles indicate that a surface has greater dirt and soil repellency, and easier surface cleanability.

Test Method 4-Wetting/Leveling Test

To test the performance of the samples in their wetting and leveling ability, the samples were added to a floor polish (RHOPLEX 3829, Formulation N-29-1, available from The Dow Chemical Company, Philadelphia, Pa.]) and applied to half of a thoroughly cleaned 12 inch×12 inch (30.36 cm×30.36 cm) vinyl tile (available from Interfuse Vinyl Tiles by Estrie, Sherbrooke, QC Canada). The tiles are thoroughly cleaned by wetting the tiles, adding a powdered oxygen bleach cleanser and scrubbing using a green SCOTCH-BRITE scouring pad, available from 3M Company, St. Paul Minn.). This scrubbing procedure was used to remove the pre-existing coating on the tiles. The tiles initially have a uniform shiny finish; a uniform dull finish indicates coating removal. The tiles are then air-dried overnight. A 1 wt % solution of the surfactant to be tested was prepared by dilution in deionized water. Following the resin manufacturer protocols, a 100 g portion of the RHOPLEX 3829, N-29-1 formulation was prepared, followed by addition of 0.75 g of the 1 wt % surfactant solution, to provide a test floor polish.

The test floor polish was applied to the tile by placing 3 mL portion of the test polish in the center of the tile, and spreading from top to bottom using a cheesecloth applicator, and finally placing a large "X" across the tile, using the applicator. The "X" subsequently provides visual evidence of leveling at the rating step. The applicator was prepared from a two-layer 18×36 inch (46×91 cm) sheet of cheesecloth (from VWR, West Chester Pa.), folded twice into an eight-layer pad. One corner of the pad was then used as the applicator. The tile was allowed to dry for 30 min. and a total of 5 coats (Coating #s 1-5) were applied and dried, with the X test performed after each coating had been dried. After each coat, the tile was rated on a 1 to 5 scale (1 being the worst, 5 the best) on the surfactant's ability to promote wetting and leveling of the polish on the tile surface. The rating is determined using the Tile Rating Scale (Table 4), based on comparison of a tile treated with the floor polish that contains no added surfactant.

TABLE 2

Visual Tile Rating Scale for Leveling

| Rating | Description |
|---|---|
| 1 | Uneven surface coverage of the film, significant streaking and surface defects |
| 2 | Numerous surface defects and streaks are evident but, generally, film coats entire tile surface |
| 3 | Visible streaking and surface defects, withdrawal of the film from the edges of the tile |

TABLE 2-continued

Visual Tile Rating Scale for Leveling

| Rating | Description |
|---|---|
| 4 | Minor surface imperfections or streaking |
| 5 | No visible surface defects or streaks |

Materials

Unless otherwise noted, all of the chemicals used herein are commercially available from Sigma Aldrich, St. Louis, Mo.

2,2,3,3,3-pentafluoropropanol is commercially available from Oakwood Products Inc.

2,2,3,3,4,4,4-heptafluorobutan-1-ol is commercially available from Oakwood Products Inc.

Triphosgene is commercially available from TCI America.

Phosphorus Pentoxide is commercially available from Filo Chemical or from Changzhou Qishuyan Fine Chemical CO., LTD.

MAB paints have an acrylic semi-gloss resin with 84% gloss at 85 degrees and are commercially available from M. A. Bruder and Sons, Inc., Broomall, Pa.

EXAMPLES

Examples 1-3 illustrate the preparation of phosphate compounds of the present invention from $C_2F_5CH_2OCF_2CF_2CH_2OH$.

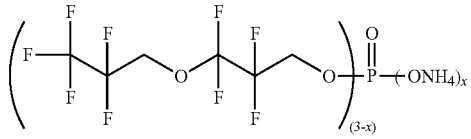

Example 1

Triphosgene (24.5 g, 82.5 mmol) and anhydrous diethyl ether (~400 mL) were added to a 1-L 4-neck flask. The mixture was cooled to 0° C., and 2,2,3,3,3-pentafluoropropanol (75 g, 0.50 mol) was added. Pyridine (40.0 g, 0.51 mol) was then slowly added at 0° C. to the mixture. The resultant mixture was then refluxed for 1 hour. The solution was filtered to remove white solids and washed with dilute hydrochloric acid solution. The solution was then vacuum distilled to remove ether resulting in bis(2,2,3,3,3-pentafluoropropyl) carbonate $(CF_3CF_2CH_2O)_2CO$ (71 g, 88% yield).

A catalyst was prepared by slow addition of 2,2,3,3,3-pentafluoropropan-1-ol (15.0 g, 100 mmol) to a suspension of sodium hydride (60% in mineral oil, 6.0 g, 150 mmol) in anhydrous tetrahydrofuran (300 mL) in a 500-mL flask. The resultant mixture was stirred for 15 minutes, transferred into a Hastelloy vessel (1 L), and cooled to −20° C. The bis(2,2,3,3,3-pentafluoropropyl) carbonate, $(CF_3CF_2CH_2O)_2CO$, (115 g, 353 mmol) was then added to the vessel. The vessel was pressurized with tetrafluoroethylene (60 g, 600 mmol), and the contents were warmed to room temperature and agitated for 6 hours. The reaction mixture was then treated with a solution of NaOH (15 g, 375 mmol) in water (100 mL). Tetrahydrofuran and water were removed to vacuum, and the resultant solids were dissolved by addition of 3.0 M hydrochloric acid (400 mL). The organic phase was separated and purified via distillation to yield 2,2,3,3-tetrafluoro-3-(2,2,3,3-pentafluoropropoxy)propanoic acid $C_2F_5CH_2OCF_2CF_2C(O)OH$ (60 g, 58% yield).

$C_2F_5CH_2OCF_2CF_2C(O)OH$ (65 g, 220 mmol), ethanol (50 mL, excess), and concentrated sulfuric acid (50 g) were added to a 250 mL round bottom flask. The resultant mixture was refluxed for three hours under atmosphere of nitrogen. The product mixture was slowly added to water (400 mL), the organic layer was separated, washed with water (2×50 mL), and dried over magnesium sulfate ($MgSO_4$) to yield ethyl 2,2,3,3-tetrafluoro-3-(2,2,3,3,3-pentafluoropropoxy)propanoate $C_2F_5CH_2OCF_2CF_2C(O)OCH_2CH_3$ (70 g, 98% yield).

Lithium aluminum hydride (5.2 g, 137 mmol) and anhydrous ether (100 mL) were added to a 250-mL round bottom flask and the mixture was cooled to 5° C. $C_2F_5CH_2OCF_2CF_2C(O)OCH_2CH_3$ (77 g, 240 mmol) was added dropwise keeping the temperature between 5 and 20° C. The mixture was then washed with diluted hydrochloric acid solution, and the organic phase was separated. The organic phase was purified via distillation to yield 2,2,3,3-tetrafluoro-3-(2,2,3,3,3-pentafluoropropoxy)propan-1-ol $C_2F_5CH_2OCF_2CF_2CH_2OH$ (57 g, 85% yield).

Phosphorus pentoxide (1.5 g, 10.6 mmol) was added to 2,2,3,3-tetrafluoro-3-(2,2,3,3,3-pentafluoropropoxy)propan-1-ol (8.0 g, 28.6 mmol) under atmosphere of nitrogen. The resultant mixture was heated at 85° C. for 4 hours to give a mixed phosphate acid as a yellow viscous liquid. This mixed phosphate acid was neutralized with aqueous ammonium hydroxide solution to a pH 7.7±0.5 to produce an aqueous solution of mixed phosphate ammonium salt of the formula above where x is 1 to 2. A solution of the mixed phosphate ammonium salt in water was prepared with 15% solids and tested according to the test methods as described above.

Example 2

The preparation according to Example 1 was followed, except the mixed phosphate acid was neutralized with aqueous ammonium hydroxide in a water/isopropanol solution (80/20) to form a mixture at 30% solids. The resulting solution was tested according to the test methods as described above.

Example 3

The preparation according to Example 1 was followed, except the mixed phosphate acid was neutralized with L-lysine in a water/isopropanol solution (80/20) to form a mixture at 33% solids. The resulting solution was tested according to the test methods as described above.

Examples 4-5 illustrate the preparation of phosphate compounds of the present invention from $C_3F_7CH_2CF_2CF_2CH_2OH$.

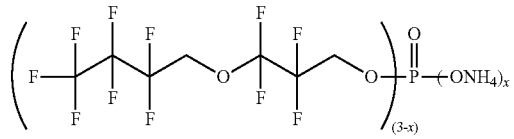

Example 4

Anhydrous ether (180 mL), methyl chloroformate (50 g, 530 mmol), and 2,2,3,3,4,4,4-heptafluorobutan-1-ol (100 g, 500 mmol) were added to a 500-mL round bottom flask. The mixture was stirred at ambient temperature for 30 minutes. Then pyridine (42 g, 530 mmol) was added dropwise with stirring, keeping the temperature between 5 and 15° C. More methyl chloroformate (18.0 g, 190 mmol) was added to the mixture followed by the addition of more pyridine (15 g, 190 mmol) at 5-15° C. The reaction mixture was washed with a 2 M solution of hydrochloric acid in water (200 mL) and the organic phase was collected. The organic phase was purified via distillation to yield 2,2,3,3,4,4,4-heptafluorobutyl methyl carbonate $C_3F_7CH_2OC(O)OCH_3$ (91 g, 71% yield).

Sodium hydride (60% in mineral oil, 2.4 g, 60 mmol) and anhydrous tetrahydrofuran (120 mL) were added to a 250-mL flask under nitrogen atmosphere. Then 2,2,3,3,4,4,4-heptafluorobutan-1-ol (10 g, 50 mmol) was slowly added. The mixture was stirred at 20° C. for 15 minutes and then transferred to a 400-mL Hastelloy vessel, at which point the mixture was cooled to −30° C. and $C_3F_7CH_2OC(O)OCH_3$ (30 g, 116 mmol) was added to the vessel. The vessel was then pressurized with tetrafluoroethylene (20 g, 200 mmol), allowed to warm to ambient temperature, agitated for 3 hours, and then vented. The mixture was transferred to a 250-mL flask, cooled to 0° C., and lithium aluminum hydride (2.4 g, 63 mmol) was added. The mixture was stirred for 3 hours at a temperature between 5 and 20° C., and the resultant mixture was washed with a 1 M solution of hydrochloric acid in water (200 mL). The organic phase was isolated and tetrahydrofuran was removed to vacuum. The remaining organic phase was purified via distillation to yield 2,2,3,3-tetrafluoro-3-(2,2,3,3,4,4,4-heptafluorobutoxy)propan-1-ol $C_3F_7CH_2CF_2CF_2CH_2OH$ (3 g, 8% yield).

Phosphorus pentoxide (2.63 g, 18.5 mmol) was added to $C_3F_7CH_2CF_2CF_2CH_2OH$ (16.5 g, 50 mmol) under atmosphere of nitrogen. The resultant mixture was heated at 85° C. for 4 hours to give a mixed phosphate acid as a yellow viscous liquid. This mixed phosphate acid was neutralized with aqueous ammonium hydroxide solution to a pH 8.0±0.5 to produce an aqueous solution of mixed phosphate ammonium salt of the formula above where x is 1 to 2. A solution of the mixed phosphate ammonium salt in water was prepared with 14% solids and tested according to the test methods as described above.

Example 5

The preparation according to Example 4 was followed, except the mixed phosphate acid was neutralized with aqueous ammonium hydroxide in a water/isopropanol solution (80/20) to form a mixture at 34% solids. The resulting solution was tested according to the test methods as described above.

Comparative Examples A and B illustrate the preparation of phosphate compounds from $CF_3CF_2CF_2CH_2OH$.

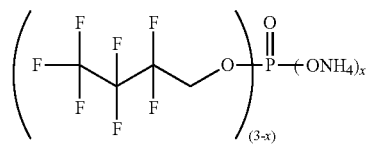

Comparative Example A

Phosphorus pentoxide (6.57 g, 46.3 mmol) was added to 2,2,3,3,4,4,4-heptafluorobutan-1-ol $CF_3CF_2CF_2CH_2OH$ (25 g, 125 mmol) under atmosphere of nitrogen. The resultant mixture was heated at 80° C. for 4 hours to give a mixed phosphate acid as a brown viscous liquid. This mixed phosphate acid was neutralized with aqueous ammonium hydroxide solution to a pH 7.7±0.3 to produce an aqueous solution of mixed phosphate ammonium salt of the formula above where x is 1 to 2. A solution of the mixed phosphate ammonium salt in water was prepared with 14% solids and tested according to the test methods as described above.

Comparative Example B

The preparation according to Comparative Example A was followed, except the mixed phosphate acid was neutralized with aqueous ammonium hydroxide in a water/isopropanol solution (80/20) to form a mixture at 35% solids. The resulting solution was tested according to the test methods as described above.

TABLE 3

Anti-blocking and Leveling Ratings with Advancing Contact Angles

| Ex. | Blocking Rating (at 200 ppm of active ingredient) | Leveling Rating | Contact Angle in Water (deg) (at 200 ppm of active ingredient) | Contact Angle in Oil (deg) (at 200 ppm of active ingredient) |
|---|---|---|---|---|
| A | 6.2 | — | 52 | 56 |
| B | 6.5 | 1.4 | 68 | 62 |
| 4 | 8.7 | 2.9 | 77 | 75 |
| 5 | 8.0 | — | 71 | 76 |
| Blank | 3.0 | 1.1-1.6 | 63 | 0 |

Table 3 shows a direct comparison of phosphates made with a short-chain fluorinated alcohol $C_3F_7CH_2OH$ (Comparative Examples A and B) and phosphates made with $C_3F_7CH_2OCF_2CF_2CH_2OH$ according to the invention (Examples 4 and 5). The phosphates according to the present invention provided superior blocking resistance, leveling, and contact angles to the coated substrates when compared to the short-chain fluorinated phosphates of Comparative Examples A and B.

Examples 6-7 illustrate the preparation of phosphate compounds of the present invention from $C_3F_7CH_2OCH_2CH_2CH_2OH$.

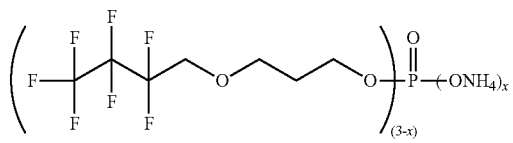

Example 6

Sodium hydride (60% in mineral oil, 5.0 g, 124 mmol) and anhydrous tetrahydrofuran (80 mL) were charged into a 250 mL flask, and 2,2,3,3,4,4,4 heptafluorobutan-1-ol (22.0 g, 110 mmol) was slowly added. Next, 3-bromopropan-1-ol (10.5 g, 76 mmol) was added, and the resultant mixture was heated at 50° C. for 3 hours. The reaction mixture was washed with 0.5 M solution of hydrochloric acid in water (100 mL), and the organic layer was isolated. The organic layer was distilled to yield 3-(2,2,3,3,4,4,4 heptafluorobutoxy)propan-1-ol $C_3F_7CH_2OCH_2CH_2CH_2OH$ (10 g, or 51% yield).

Phosphorus pentoxide (2.22 g, 15.6 mmol) was added to 3-(2,2,3,3,4,4,4-heptafluorobutoxy)propan-1-ol (11 g, 42 mmol) under atmosphere of nitrogen. The resultant mixture was heated at 70° C. for 4 hours to give a mixed phosphate acid as a yellow viscous liquid. This mixed phosphate acid was neutralized with aqueous ammonium hydroxide solution to a pH 8.0±0.3 to produce an aqueous solution of mixed phosphate ammonium salt of the formula above where x is 1 to 2. A solution of the mixed phosphate ammonium salt in water was prepared with 14% solids and tested according to the test methods as described above.

Example 7

The preparation according to Example 6 was followed, except the mixed phosphate acid was neutralized with aqueous ammonium hydroxide in a water/isopropanol solution (80/20) to form a mixture at 35% solids. The resulting solution was tested according to the test methods as described above.

Examples 8-9 illustrate the preparation of phosphate compounds of the present invention from $C_3F_7CH_2OCH_2CH_2OCH_2CH_2OH$.

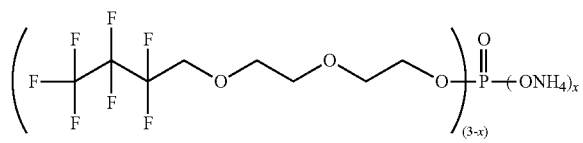

Example 8

Sodium hydride (60% in mineral oil, 6.0 g, 150 mmol) and anhydrous diglyme (80 mL) were charged into a 250-mL flask, and 2,2,3,3,4,4,4-heptafluorobutan-1-ol (30.0 g, 150 mmol) was slowly added. Next, 2-(2-chloroethoxy)ethanol (12.4 g, 100 mmol) was added, and the resultant mixture was heated at 110° C. for 2 hours. The reaction mixture was washed with 0.5 M solution of hydrochloric acid in water (100 mL), and the organic layer was isolated. The organic layer was distilled to yield 2-(2-(2,2,3,3,4,4,4-heptafluorobutoxy)ethoxy)ethanol $C_3F_7CH_2OCH_2CH_2OCH_2CH_2OH$ (10 g, 35% yield).

Phosphorus pentoxide (1.85 g, 13 mmol) was added to 2-(2-(2,2,3,3,4,4,4-heptafluorobutoxy)ethoxy)ethanol (9.9 g, 34 mmol) under atmosphere of nitrogen. The resultant mixture was heated at 75° C. for 4 hours to give a mixed phosphate acid as a yellow viscous liquid. This mixed phosphate acid was neutralized with aqueous ammonium hydroxide solution to a pH 7.8±0.2 to produce an aqueous solution of mixed phosphate ammonium salt of the formula above where x is 1 to 2. A solution of the mixed phosphate ammonium salt in water was prepared with 13% solids and tested according to the test methods as described above.

Example 9

The preparation according to Example 8 was followed, except the mixed phosphate acid was neutralized with aqueous ammonium hydroxide in a water/isopropanol solution (80/20) to form a mixture at 35% solids. The resulting solution was tested according to the test methods as described above.

Examples 10-11 illustrate the preparation of phosphate compounds of the present invention from $C_3F_7CH_2$—O—$(CH_2)_6OH$.

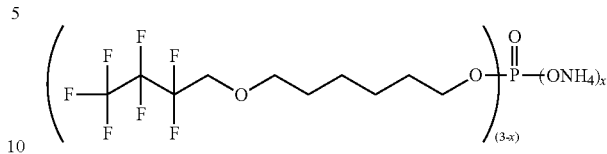

Example 10

Sodium hydride (60% in mineral oil, 6.0 g, 150 mmol) and anhydrous monoglyme (100 mL) were charged into a 250-mL flask, and 2,2,3,3,4,4,4-heptafluorobutan-1-ol (30.0 g, 150 mmol) was slowly added. Next, 6-bromohexan-1-ol (21.0 g, 116 mmol) was added, and the resultant mixture was heated at reflux for 4 hours. The reaction mixture was washed with 1 M solution of hydrochloric acid in water (30 mL) and the organic layer was isolated. The organic layer was distilled to yield 6-(2,2,3,3,4,4,4-heptafluorobutoxy)hexan-1-ol $C_3F_7CH_2$—O—$(CH_2)_6OH$ (20.6 g, 59% yield).

Phosphorus pentoxide (1.73 g, 12.3 mmol) was added to 6-(2,2,3,3,4,4,4-heptafluorobutoxy)hexan-1-ol (10 g, 33 mmol) under atmosphere of nitrogen. The resultant mixture was heated at 90° C. for 4 hours to give a mixed phosphate acid as a yellow viscous liquid. This mixed phosphate acid was neutralized with aqueous ammonium hydroxide solution to a pH 8.0±0.5 to produce an aqueous solution of mixed phosphate ammonium salt of the formula above where x is 1 to 2. A solution of the mixed phosphate ammonium salt in water was prepared with 12% solids and tested according to the test methods as described above.

Example 11

The preparation according to Example 10 was followed, except the mixed phosphate acid was neutralized with aqueous ammonium hydroxide in a water/isopropanol solution (80/20) to form a mixture at 35% solids. The resulting solution was tested according to the test methods as described above.

Examples 12-13 illustrate the preparation of phosphate compounds from $CF_3CF_2CF_2CH_2OCH_2CH_2OH$.

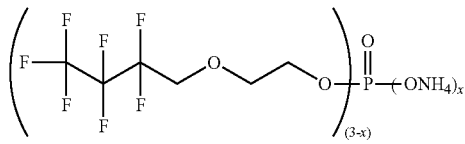

Example 12

Sodium hydroxide (2.0 g, 50 mmol), anhydrous monoglyme (170 mL), and 2,2,3,3,4,4,4-heptafluorobutan-1-ol (70 g, 350 mmol) were charged into a Hastelloy vessel (400 mL). The vessel was pressurized with ethylene oxide (15 g, 340 mmol) and heated at 90° C. for 16 hours. The reaction mixture was washed with 0.5 M solution of hydrochloric acid in water (50 mL), and the organic layer was isolated. The organic layer was distilled to yield 2-(2,2,3,3,4,4,4-heptafluorobutoxy)ethanol $CF_3CF_2CF_2CH_2OCH_2CH_2OH$ (61 g, 71% yield).

Phosphorus pentoxide (2.59 g, 18.2 mmol) was added to 2-(2,2,3,3,4,4,4-heptafluorobutoxy)ethanol $CF_3CF_2CF_2CH_2OCH_2CH_2OH$ (11.8 g, 48.3 mmol) under atmosphere of nitrogen. The resultant mixture was heated at 90° C. for 4 hours to give a mixed phosphate acid as a brown viscous liquid. This mixed phosphate acid was neutralized with aqueous ammonium hydroxide solution to a pH 8.0±0.2 to produce an aqueous solution of mixed phosphate ammonium salt of the formula above where x is 1 to 2. A solution of the mixed phosphate ammonium salt in water was prepared with 11% solids and tested according to the test methods as described above.

Example 13

The preparation according to Example 12 was followed, except the mixed phosphate acid was neutralized with aqueous ammonium hydroxide in a water/isopropanol solution (80/20) to form a mixture at 33% solids. The resulting solution was tested according to the test methods as described above.

TABLE 4

Anti-blocking and Leveling Ratings with Advancing Contact Angles

| Ex. | Blocking Rating at 77 ppm of Fluorine | Leveling Rating | Contact Angle in Water (deg) at 77 ppm of Fluorine | Contact Angle in Oil (deg) at 77 ppm of Fluorine |
|---|---|---|---|---|
| A | 5.3 | — | 74 | 53 |
| B | 6.0 | 1.4 | 66 | 48 |
| 6 | 7.2 | — | 68 | 71 |
| 7 | 7.7 | 3.2 | 76 | 65 |
| 8 | 6.7 | — | 82 | 69 |
| 9 | 7.0 | 2.7 | 82 | 66 |
| 10 | 7.7 | — | 63 | 71 |
| 11 | 8.7 | 3.2 | 55 | 69 |
| 12 | 7.2 | — | 68 | 71 |
| 13 | 7.7 | 2.7 | 62 | 72 |
| Blank | 1.2 | 1.1 | 71 | 0 |

Table 4 shows a direct comparison of phosphates made with a short-chain fluorinated alcohol $C_3F_7CH_2OH$ (Comparative Examples A and B), a fluorinated alcohol extended with a —$CH_2CH_2$— group $C_3F_7CH_2OCH_2CH_2OH$ according to the invention (Examples 12 and 13), phosphates made with a $C_3$ hydrocarbon extender $C_3F_7CH_2OCH_2CH_2CH_2OH$ according to the invention (Examples 6 and 7), phosphates made with a $C_6$ hydrocarbon extender according to the invention (Examples 10 and 11), and phosphates made with an ether extender $C_3F_7CH_2OCH_2CH_2OCH_2CH_2OH$ (Examples 8 and 9). All phosphates based on extended alcohols provided superior blocking resistance, leveling, and oil contact angles to the coated substrates when compared to the short-chain fluorinated phosphates of Comparative Examples A and B.

Examples 14-15 illustrate the preparation of phosphate compounds of the present invention from $C_2F_5CH_2OCF_2CF_2CH_2$—O—$(CH_2)_3OH$.

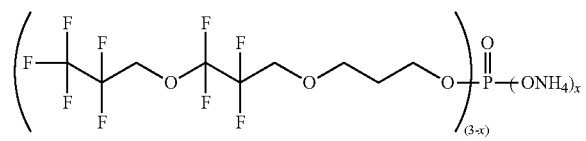

Example 14

2,2,3,3-tetrafluoro-3-(2,2,3,3,3-pentafluoropropoxy)propan-1-ol $C_2F_5CH_2OCF_2CF_2CH_2OH$ was prepared as in Example 1. Sodium hydride (60% in mineral oil, 4.4 g, 110 mmol) and anhydrous tetrahydrofuran (80 mL) were charged into a 250-mL flask, and $C_2F_5CH_2OCF_2CF_2CH_2OH$ (18.0 g, 64 mmol) was slowly added. Then, 3-bromopropan-1-ol (8.0 g, 58 mmol) was added, and the resultant mixture was heated at 60° C. for 4 hours. The mixture was washed with 0.5 M solution of hydrochloric acid in water (100 mL), and the organic layer was isolated. The organic material was distilled to yield 342,2,3,3-tetrafluoro-3-(2,2,3,3,3-pentafluoropropoxy)propoxy)-propan-1-ol $C_2F_5CH_2OCF_2CF_2CH_2$—O—$(CH_2)_3OH$ (8.5 g, 43% yield).

Phosphorus pentoxide (1.58 g, 11.1 mmol) was added to 342,2,3,3-tetrafluoro-3-(2,2,3,3,3-pentafluoropropoxy)propoxy)-propan-1-ol (10.5 g, 31 mmol) under atmosphere of nitrogen. The resultant mixture was heated at 80° C. for 9 hours to give a mixed phosphate acid as a yellow viscous liquid. This mixed phosphate acid was neutralized with aqueous ammonium hydroxide solution to a pH 7.8±0.2 to produce an aqueous solution of mixed phosphate ammonium salt of the formula above where x is 1 to 2. A solution of the mixed phosphate ammonium salt in water was prepared with 15% solids and tested according to the test methods as described above.

Example 15

The preparation according to Example 14 was followed, except the mixed phosphate acid was neutralized with aqueous ammonium hydroxide in a water/isopropanol solution (80/20) to form a mixture at 34% solids. The resulting solution was tested according to the test methods as described above.

Comparative Example C illustrates the preparation of phosphate compounds of the present invention from $CF_3CF_2CF_2CF_2CH_2OH$.

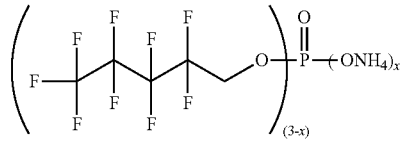

Comparative Example C

Phosphorus pentoxide (2.84 g, 20 mmol) was added to 2,2,3,3,4,4,5,5,5-nonafluoropentan-1-ol $CF_3CF_2CF_2CF_2CH_2OH$ (14.0 g, 56 mmol) under atmosphere of nitrogen. The resultant mixture was heated at 78° C. for 6 hours to give a mixed phosphate acid as a yellow viscous liquid. This mixed phosphate acid was neutralized with aqueous ammonium hydroxide solution to a pH 7.5±0.3 to produce an aqueous solution of mixed phosphate ammonium salt of the formula above where x is 1 to 2. A solution of the mixed phosphate ammonium salt in water was prepared with 15% solids and tested according to the test methods as described above.

Comparative Example D

The preparation according to Comparative Example C was followed, except the mixed phosphate acid was neutralized with aqueous ammonium hydroxide in a water/isopropanol solution (80/20) to form a mixture at 33% solids. The resulting solution was tested according to the test methods as described above.

TABLE 5

Anti-blocking and Leveling Ratings with Advancing Contact Angles

| Ex. | Blocking Rating at 110 ppm of Fluorine | Leveling Rating | Contact Angle in Water (deg) at 110 ppm of Fluorine | Contact Angle in Oil (deg) at 110 ppm of Fluorine |
|---|---|---|---|---|
| C | 7.0 | 2.7 | 86 | 70 |
| D | 6.3 | 3.0 | 85 | 70 |
| 1 | 6.8 | 3.0 | 87 | 60 |
| 2 | 6.0 | 2.6 | 82 | 58 |
| 3 | 6.3 | 2.8 | 84 | 61 |
| 14 | 7.8 | 3.0 | 84 | 71 |
| 15 | 7.2 | 2.6 | 86 | 70 |
| Blank | 0 | 1.2 | 70 | 0 |

Table 5 shows a direct comparison of phosphates made with a short-chain fluorinated alcohol $C_4F_9CH_2OH$ (Comparative Examples C and D), phosphates made with a fluorinated alcohol interrupted with a fluoroalkyl group $C_2F_5CH_2OCF_2CF_2CH_2OH$ (Examples 1-3), and phosphates made with a fluorinated alcohol extended with a $C_3$ hydrocarbon extender $C_2F_5CH_2OCF_2CF_2CH_2OCH_2CH_2CH_2OH$ according to the invention (Examples 14 and 15). In this case, the phosphates of the invention have the same number of fluorine atoms but lower overall fluorine content than the phosphates of the comparative examples. The phosphates of the invention based on extended alcohols (Examples 14 and 15) provided equal or superior performance to the phosphates of Comparative Examples C and D at the same fluorine level, while employing partially fluorinated alcohols made from a new, more selective and efficient synthetic process.

Example 16 illustrates the preparation of phosphate compounds of the present invention from $C_2F_5CH_2OCF_2CF_2CH_2OCH_2CH_2OH$.

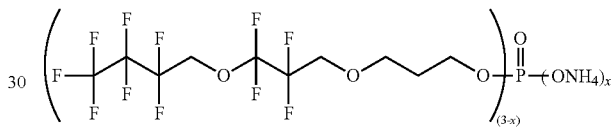

Example 16

2,2,3,3-tetrafluoro-3-(2,2,3,3,3-pentafluoropropoxy)propan-1-ol $C_2F_5CH_2OCF_2CF_2CH_2OH$ was prepared as in Example 1. Boric acid (0.3 g, 5 mmol) and $C_2F_5CH_2OCF_2CF_2CH_2OH$ (31.4 g, 112 mmol) were charged into a 100-mL flask equipped with a 10-mL Dean-Stark condenser, and the mixture was heated at 125° C. for 1 hour. The mixture was then transferred into a Hastelloy vessel (400 mL), and tetrabutylammonium iodide (1.5 g, 4 mmol) was added. The vessel was pressurized with ethylene oxide (5 g, 114 mmol) and heated at 110° C. for 6 hours. At this point, the mixture was transferred to a 100-mL flask, a solution of sodium hydroxide (3.0 g, 75 mmol) in water (30 mL) was added, and the mixture was stirred at 70° C. for 20 minutes. The mixture was cooled, the organic phase was separated, and the product was distilled to yield 242,2,3,3-tetrafluoro-3-(2,2,3,3,3-pentafluoropropoxy)propoxy)-ethanol $C_2F_5CH_2OCF_2CF_2CH_2OCH_2CH_2OH$ (4.4 g, 19% yield).

Phosphorus pentoxide (0.67 g, 4.7 mmol) was added to 242,2,3,3-tetrafluoro-3-(2,2,3,3,3-pentafluoropropoxy)propoxy)-ethanol (4.3 g, 13.3 mmol) under atmosphere of nitrogen. The resultant mixture was heated at 70° C. for 4 hours to give a mixed phosphate acid as a yellow viscous liquid. This mixed phosphate acid was neutralized with aqueous ammonium hydroxide solution to a pH 7.8±0.2 to produce an aqueous solution of mixed phosphate ammonium salt of the formula above where x is 1 to 2. A solution of the mixed phosphate ammonium salt in water was prepared with 10% solids and tested according to the test methods as described above.

Examples 17 illustrates the preparation of phosphate compounds of the present invention from $C_3F_7CH_2OCF_2CF_2CH_2-O-(CH_2)_3OH$.

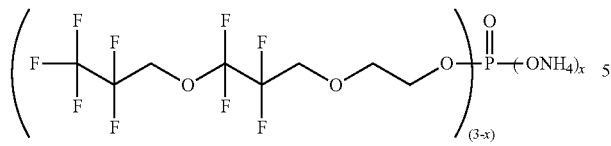

Example 17

2,2,3,3-tetrafluoro-3-(2,2,3,3,4,4,4-heptafluorobutoxy)propan-1-ol $C_3F_7CH_2CF_2CF_2CH_2OH$ was prepared as in Example 4. Sodium hydride (60% in mineral oil, 3.2 g, 80 mmol) and anhydrous tetrahydrofuran (80 mL) were charged into a 250-mL flask, and $C_3F_7CH_2CF_2CF_2CH_2OH$ (25 g, 76 mmol) was slowly added. The resultant mixture was stirred for 10 minutes, and 3-bromopropan-1-ol (9.5 g, 68 mmol) was added. The resultant mixture was heated at 50° C. for 8 hours, then washed with 0.5 M solution of hydrochloric acid in water (100 mL). The organic layer was isolated and distilled to yield 3-(2,2,3,3-tetrafluoro-3-(2,2,3,3,4,4,4-heptafluorobutoxy)propoxy)-propan-1-ol $C_3F_7CH_2OCF_2CF_2CH_2-O-(CH_2)_3OH$ (12.4 g, 47% yield).

Phosphorus pentoxide (1.63 g, 11.5 mmol) was added to 3-(2,2,3,3-tetrafluoro-3-(2,2,3,3,4,4,4-heptafluorobutoxy)propoxy)-propan-1-ol (12 g, 31 mmol) under atmosphere of nitrogen. The resultant mixture was heated at 80° C. for 3 hours to give a mixed phosphate acid as a yellow viscous liquid. This mixed phosphate acid was neutralized with aqueous ammonium hydroxide solution to a pH 8.8±0.2 to produce an aqueous solution of mixed phosphate ammonium salt of the formula above where x is 1 to 2. A solution of the mixed phosphate ammonium salt in water was prepared with 13% solids and tested according to the test methods as described above.

TABLE 6

| | Surface Tension in Deionized Water at 25° C. (dyne/cm) | | | | | | | | | |
|---|---|---|---|---|---|---|---|---|---|---|
| | Weight % of Active Ingredient (by Solids) × $10^{-2}$ | | | | | | | | | |
| Ex. | 0.1 | 0.25 | 0.5 | 1 | 2.5 | 5 | 10 | 20 | 25 | 40 | 50 |
| B | 71.1 | 70.5 | 69.6 | 67.3 | 63.5 | 59.4 | 53.7 | | 45.7 | | 39.2 |
| C | 68.2 | 64.4 | 60.9 | 56.9 | 49.4 | 42.5 | 35.2 | | 25.7 | | 18.2 |
| 2 | 69.1 | 65.1 | 62.3 | 58.4 | 51.3 | 45.0 | 37.9 | | 29.5 | | 21.8 |
| 6 | 69.4 | 67.1 | 62.8 | 56.8 | 50.8 | 44.2 | 36.9 | | 28.8 | | 20.4 |
| 9 | 67.9 | 65.7 | 61.5 | 55.7 | 47.2 | 41.5 | 34.2 | 29.1 | | 23.3 | |
| 11 | 57.1 | 51.6 | 46.7 | 40.5 | 32.5 | 24.9 | 19.3 | | 18.2 | | 18.1 |
| 12 | 68.5 | 65.2 | 61.9 | 54.8 | 42.8 | 37.2 | 30.4 | | 23.1 | | 17.7 |
| 14 | 49.8 | 42.9 | 39.3 | 35.4 | 30.7 | 27.4 | 25.0 | | 19.1 | | 18.6 |
| 16 | 54.9 | 49.4 | 44.9 | 39.8 | 34.5 | 30.9 | 24.3 | | 18.5 | | |
| 17 | 54.5 | 44.6 | 38.6 | 31.2 | 22.2 | 17.9 | 17.0 | | | | |

Table 6 shows a direct comparison of phosphates made with short-chain fluorinated alcohols $C_3F_7CH_2OH$ and $C_4F_9CH_2OH$ (Comparative Examples B and C, respectively) compared to the phosphates made according to the present invention. The phosphates of the invention provided superior surface tension when compared with Comparative Example B. Additionally, the phosphates of the invention provided equal or superior performance to the phosphates of Comparative Example C, while employing partially fluorinated alcohols made from a new, more selective and efficient synthetic process.

What is claimed is:

1. A compound of formula (1), or mixtures thereof:

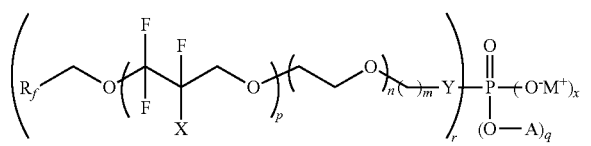

(1)

wherein
$R_f$ is $C_1$ to $C_6$ linear or branched fluoroalkyl,
X is F or Cl,
Y is O or a single bond,
A is —$R^1$OH or $ZR^2$,
p is 0 to 1,
m is 0 or 2 to 10,
n is 0 to 30,
r is 1 or (3−x),
q is 0 or 1,
x is 1 to 2,
M is H, a Group I metal, an ammonium alkanol, an ammonium cation $(NH_zR^3_y)^+$, or an ammonium cation $(NH_2R^4R^5)^+$; wherein $R^3$ is a $C_1$ to $C_4$ alkyl, z is 1 to 4, y is 0 to 3, z+y is 4; $R^4$ and $R^5$ are independently H or linear or branched organic groups containing at least one carboxylate moiety and one amino moiety, and $R^4$ and $R^5$ are independently optionally substituted, interrupted, or both with oxygen, sulfur, or nitrogen-containing moieties, or with cyclic, alkyl, or aryl moieties containing up to 10 carbon atoms,
$R^1$ is a $C_2$ to $C_{60}$ linear or branched alkylene group optionally interrupted by hetero atoms selected from the group consisting of an oxygen, sulfur, or nitrogen atom; a cyclic alkyl; or a $C_6$ to $C_{10}$ aryl;
$R^2$ is a linear, branched, or cyclic alkyl or a $C_6$ to $C_{10}$ aryl,
Z is —$(CH_2CHR^6O)_a$,
a is 1 to 20,
$R^6$ is H, $CH_3$, or $CH_2CH_3$,
wherein at least one of p or m is a positive integer,
provided that, when q is 0, r is (3−x), and when q is 1, r and x are each 1;
provided that, if n is greater than 2, then p is 1;
provided that, if m is 0 then Y is a single bond, and if m is a positive integer then Y is O; and
provided that when $R^1$ is greater than 8 carbons, the ratio of hetero atoms to carbon atoms is at least 1:2.

2. The compound of claim 1, wherein $R_f$ is $C_1$ to $C_3$ linear fluoroalkyl.

3. The compound of claim 1 selected from the formula (1) such that (i) p is 1, m is 0 or 3 to 8, and n is 0; (ii) p is 0, m is 2 to 8, and n is 0; (iii) p is 1, m is 0, and n is 1 to 12; or (4) p is 0, m is 0, and n is 1 to 2.

4. A method for lowering the surface tension of coating compositions comprising contacting said coating compositions with one or more compounds of formula (1):

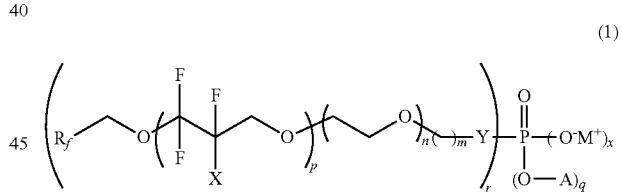

(1)

wherein
$R_f$ is $C_1$ to $C_6$ linear or branched fluoroalkyl,
X is F or Cl,
Y is O or a single bond,
A is —$R^1$OH or $ZR^2$,
p is 0 to 1,
m is 0 or 2 to 10,
n is 0 to 30,
r is 1 or (3−x),
q is 0 or 1,
x is 1 to 2,
M is H, a Group I metal, an ammonium alkanol, an ammonium cation $(NH_zR^3_y)^+$, or an ammonium cation $(NH_2R^4R^5)^+$; wherein $R^3$ is a $C_1$ to $C_4$ alkyl, z is 1 to 4, y is 0 to 3, z+y is 4; $R^4$ and $R^5$ are independently H or linear or branched organic groups containing at least one carboxylate moiety and one amino moiety, and $R^4$ and $R^5$ are independently optionally substituted, interrupted, or both with oxygen, sulfur, or nitrogen-containing moieties, or with cyclic, alkyl, or aryl moieties containing up to 10 carbon atoms, $R^1$ is a $C_2$ to $C_{60}$ linear or branched alkylene group optionally interrupted by hetero atoms selected from the group consisting of an oxygen, sulfur, or nitrogen atom; a cyclic alkyl; or a $C_6$ to $C_{10}$ aryl;

$R^2$ is a linear, branched, or cyclic alkyl or a $C_6$ to $C_{10}$ aryl,

Z is $-(CH_2CHR^6O)_a$, a is 1 to 20, $R^6$ is H, $CH_3$, or $CH_2CH_3$, wherein at least one of p or m is a positive integer, provided that, when q is 0, r is (3−x), and when q is 1, r and x are each 1;

provided that, if n is greater than 2, then p is 1;

provided that, if m is 0 then Y is a single bond, and if m is a positive integer then Y is O; and provided that when $R^1$ is greater than 8 carbons, the ratio of hetero atoms to carbon atoms is at least 1:2.

5. A method of imparting surface effects to substrates comprising contacting all or a portion of a surface of the substrate with a coating composition comprising one or more compounds of formula (1):

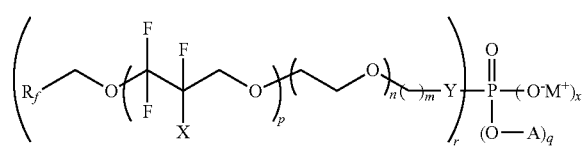

(1)

wherein $R_f$ is $C_1$ to $C_6$ linear or branched fluoroalkyl,

X is F or Cl,

Y is O or a single bond,

A is $-R^1OH$ or $ZR^2$, p is 0 to 1, m is 0 or 2 to 10, n is 0 to 30, r is 1 or (3−x), q is 0 or 1, x is 1 to 2,

M is H, a Group I metal, an ammonium alkanol, an ammonium cation $(NH_zR^3_y)^+$, or an ammonium cation $(NH_2R^4R^5)^+$; wherein $R^3$ is a $C_1$ to $C_4$ alkyl, z is 1 to 4, y is 0 to 3, z+y is 4; $R^4$ and $R^5$ are independently H or linear or branched organic groups containing at least one carboxylate moiety and one amino moiety, and $R^4$ and $R^5$ are independently optionally substituted, interrupted, or both with oxygen, sulfur, or nitrogen-containing moieties, or with cyclic, alkyl, or aryl moieties containing up to 10 carbon atoms, $R^1$ is a $C_2$ to $C_{60}$ linear or branched alkylene group optionally interrupted by hetero atoms selected from the group consisting of an oxygen, sulfur, or nitrogen atom; a cyclic alkyl; or a $C_6$ to $C_{10}$ aryl;

$R^2$ is a linear, branched, or cyclic alkyl or a $C_6$ to $C_{10}$ aryl,

Z is $-(CH_2CHR^6O)_a$, a is 1 to 20, $R^6$ is H, $CH_3$, or $CH_2CH_3$, wherein at least one of p or m is a positive integer, provided that, when q is 0, r is (3−x), and when q is 1, r and x are each 1;

provided that, if n is greater than 2, then p is 1;

provided that, if m is 0 then Y is a single bond, and if m is a positive integer then Y is O; and provided that when $R^1$ is greater than 8 carbons, the ratio of hetero atoms to carbon atoms is at least 1:2.

6. The method of claim 4 or 5 wherein $R_f$ is $C_1$ to $C_3$ linear fluoroalkyl.

7. The method of claim 4 or 5, wherein the compound is selected from the formula (1) such that (i) p is 1, m is 0 or 3 to 8, and n is 0; (ii) p is 0, m is 2 to 8, and n is 0; (iii) p is 1, m is 0, and n is 1 to 12; or (4) p is 0, m is 0, and n is 1 to 2.

8. The method of claim 4 or 5 wherein the coating composition is selected from the group consisting of an alkyl coating, Type I urethane coating, unsaturated polyester coating, or water-dispersed coating.

9. The method of claim 8 wherein the coating composition is a floor finish, polishing agent, floor polish, or paint.

10. The method of claim 5 wherein the surface effect is resistance to blocking, oil repellency, water repellency, stain resistance, dirt pickup resistance, increased contact angle, or increased wetting and leveling of the coating surface.

11. A method of claim 5, wherein the coating composition is applied to the substrate prior to contacting with a composition of formula (1).

12. The method of claim 4 wherein the contacting increases wetting and leveling in the coating composition.

\* \* \* \* \*